United States Patent [19]

Toyoshima et al.

[11] 4,159,321

[45] Jun. 26, 1979

[54] AGENT FOR INHIBITING TUMOR INDUCED BY LEUKEMIA VIRUS

[75] Inventors: Shigeshi Toyoshima; Mie Itoh, both of Tokyo; Syosuke Yamamura, Nagoya; Yoshiko Seto, Funabashi; Haruhisa Fujita, Kamakura; Mariko Fukuma, Musashino; Mikiro Fujiwara; Munemoto Itoh, both of Tokyo, all of Japan

[73] Assignee: Tobishi Pharmaceutical Co., Ltd., Tokyo, Japan

[21] Appl. No.: 830,746

[22] Filed: Sep. 6, 1977

[30] Foreign Application Priority Data

Sep. 13, 1976 [JP] Japan ............... 51-109648

[51] Int. Cl.$^2$ ............... C12D 9/20; C07G 11/00
[52] U.S. Cl. ............... 424/115; 195/96
[58] Field of Search ............... 195/96; 424/115

[56] References Cited

U.S. PATENT DOCUMENTS

| 3,366,540 | 1/1968 | Tendler | 424/115 |
| 3,625,833 | 12/1971 | Schaffer | 195/96 |

*Primary Examiner*—Alvin E. Tanenholtz
*Attorney, Agent, or Firm*—Bucknam and Archer

[57] ABSTRACT

A process for preparing an antimalignant agent which comprises cultivating *Staphylococcus epidermidis* STF (Bikoken(or Microbic Industry Technological Institute)Deposit No. 3706; ATCC 31310) in a liquid culture medium, removing solid matter from the culture solution, concentrating the remaining solution, washing the precipitate thus formed with water, re-dissolving the precipitate, fractionating the solution into a number of fractions by an adsorptive filtration gel or the molecular sieve method, taking a fraction exhibiting antimalignant activity, concentrating the fraction, further purifying the fraction by ion-exchange chromatography and separating the active ingredient; and the antimalignant agent thus obtained.

11 Claims, 4 Drawing Figures

I.R. SPECTRUM
5000 < M.W. < 10000

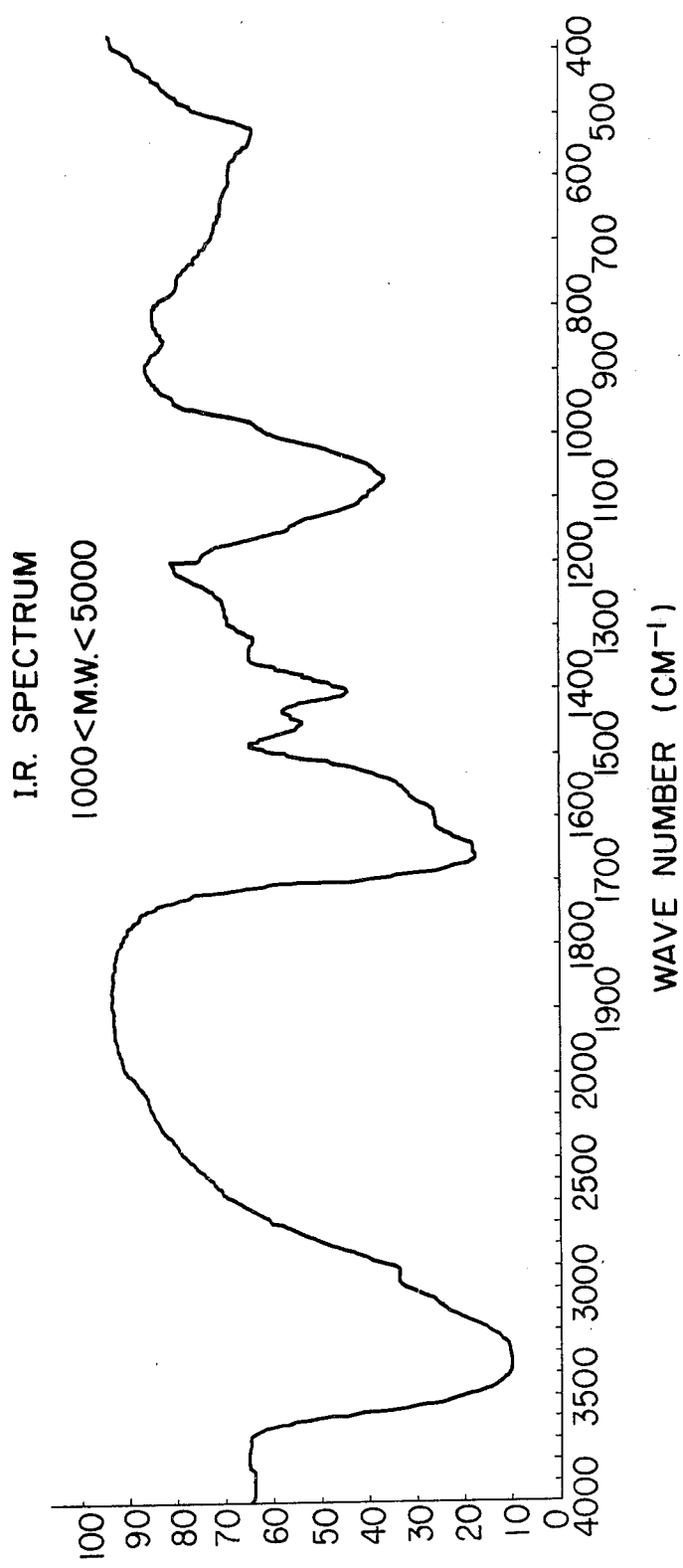

AGENT FOR INHIBITING TUMOR INDUCED BY LEUKEMIA VIRUS

BACKGROUND OF THE INVENTION

Field of the Invention

The present invention relates to a new antimalignant agent. More particularly, the present invention relates to a process for preparing a new active substance obtained by cultivating *Staphylococcus epidermidis* STF (Bikoken Deposit No. 3706; ATCC 31310) in a liquid medium.

The above substance exhibits an effect of inhibiting leukemia and malignant tumor.

The present invention is based on a finding that in a leukemia patient, leukemia cells were reduced in number remarkably unexpected when the patient developed a boil, and finally, the leucocyte number of the patient became normal.

The inventors separated a strain of microorganism from the boil of this patient, cultivated the same, administered a filtrate of the culture solution to animals affected by induced leukemia and confirmed that the administration of the filtrate gave rise to such effects on the affected animals such as reduction in amount of leukemia virus, reduction in number of leukemia cells, recovery of leukemia affected organs, prolongation of life and increase in number of surviving animals. On continuation of the investigations, the inventors have further found that said filtrate is effective not only for leukemia but also generally for other malignant tumors.

The inventors concentrated the filtrate of the culture solution, fractionated water-soluble substances considered to be active ingredients into a number of fractions and isolated and purified the substances to prove that the substances have the above described antimalignant activity.

DESCRIPTION OF THE INVENTION

Identification of the Strain

The strain of microorganism used in the present invention is a new strain. It was deposited in "Bikoken" and ATCC as Bikoken Deposit No. 3706 and ATCC 31310, respectively. The strain is freely available to all persons at these institutions. The strain was identified to be a number of the group of *Staphylococcus epidermidis* as follows:

| Primary discrimination | | |
|---|---|---|
| (1) | Motility | |
| | 37° C. | (−) |
| | 24° C. | (−) |
| (2) | Gram staining | (+) |
| (3) | Catalase activity | (+) |
| (4) | Shape | Coccus |
| (5) | Acid fast property | (−) |
| (6) | Spore formation | (−) |
| (7) | Growth in air | (+) |
| (8) | Oxidase activity | (−) |
| (9) | Glucose utilization | (+) |
| (10) | Oxidation fermentation test (Hugh-Leifson test) | F |

From the above test results, it was judged that the germ belongs to Staphylococcus or Aerococcus.

| Secondary discrimination: | | |
|---|---|---|
| (1) | Coagulase | (−) |
| (2) | V-P reaction | (+) |
| (3) | Pink reaction | (−) |
| (4) | Phosphatase | (+) |
| (5) | Nitrate reduction | (+) |

Thus, the germ was finally determined to be *Staphylococcus epidermidis*. The inventors named the strain "STF."

The germ propagates well in a common medium, i.e. a nutrient medium containing carbon, nitrogen and inorganic salts. For utilizing the useful active substance produced by the germ, an aerobic culture in a liquid medium under stationary condition or under shaking is desirable. Examples of suitable culture media will be given below:

| | | |
|---|---|---|
| (1) | Peptone | 17 g |
| | Bouillon extract | 3 g |
| | NaCl | 5 g |
| | $K_2HPO_4$ | 2.5 g |
| | Glucose | 2.5 g |
| | Distilled water | 1 liter (pH 7.3) |
| (2) | Corn steep liquor | 6 g |
| | $NH_4H_2PO_4$ | 3 g |
| | Yeast extract | 2.5 g |
| | Dextrose | 10 g |
| | $CaCO_3$ | 2.5 g |
| | Distilled water | 1 liter (pH 4.5) |

Though only liquid media are exemplified above, common solid media can also be used.

The germs were cultivated in the above medium at a culture temperature of from −20° C. to +40° C. for 24–120 hours. Optimum temperature was about 37° C. The colony surface was white and circular.

The resulting culture solution was subjected to centrifugation and the solid matter was separated out to obtain a solution (hereinafter referred to as "culture solution"). The solution was subjected to various experiments.

Utility of the Active Ingredient

The culture solution obtained was administered to animals affected by various induced diseases to obtain the following results:

(1) Inhibition of malignant tumor caused by inoculation of leukemia virus:

30 ICR Mice were divided into three groups. Two groups were inoculated with Friend's leukemia virus and thereafter 0.1 ml/10 g/day of the culture solution was intraabdominally administered to one inoculated group for eight days to obtain the following effects of inhibiting spleen hypertrophy.

| | Weight of spleen (g) | Rate of inhibition (%) |
|---|---|---|
| Uninfected group (control) | 0.124 ± 0.022 | |
| Infected group (control) | 0.724 ± 0.239 | |
| Infected group administered with the culture solution continuously for 8 days | 0.219 ± 0.039 | 84.9 |

(2) Inhibition of malignant tumor caused by inoculation of leukemia cells:

Mouse leukemia cells L-1210 were inoculated into BDF$_1$ mice to cause an induced leukemia condition. The mice dies in a limited period of time. Two groups of mice each comprising 6 mice were inoculated with L-1210 cells and, thereafter, said culture solution was administered to one of the groups continuously for five days to obtain the following results. Amount of the culture solution given was the same as in (1).

|  | Time of death (days after inoculation) |
| --- | --- |
| Untreated group | 7, 7, 7, 7, 7, 7 |
| Treated group | 7, 7, 7, 8, 8, more than 10 |

Test group/control group ratio. (life prolongation ratio) was higher than 112 (%).

(3) Effect of controlling Ehrlich cancer cells:

Two groups of ICR mice each comprising 10 mice were inoculated with Ehrlich ascites tumor cells. The culture solution was administered intraabdominally to one of the groups continuously for five days. An inhibition effect was recognized from the tumor cell numbers on the 10th day which were as shown below. Amount of the culture solution given was the same as in (1).

|  | Number of tumor cells | Rate of inhibition (%) |
| --- | --- | --- |
| Untreated group | 7.7 × 10$^8$ |  |
| Treated group | 4.7 × 10$^7$ | 93.7 |

(4) Effect of controlling Sarcoma 180 cells:

In the same manner as above, two groups of ICR mice each comprising 10 mice were inoculated with Sarcoma 180 cells intraabdominally. The culture solution was administered to one of the group continuously for five days. Cell numbers on the 10th day were examined to obtain the following results. Amount of the culture solution given was the same as in (1).

|  | Number of tumor cells | Rate of inhibition (%) |
| --- | --- | --- |
| Untreated group | 2.3 × 10$^9$ |  |
| Treated group | 5.3 × 10$^8$ | 76.9 |

For comparison, effects of culture solutions of other well-known microorganisms obtained by the same culture method were examined. Culture solutions of the following well-known microorganisms were administered to mice inoculated with Friend's leukemia virus. No effect was obtained in any of the cases:
Pseudomonas
Klebsiella
*Staphylococcus aureus*

(4) Isolation and Purification of Active Ingredient

The active ingredient contained in the culture solution of Staphylococcus epidermidis can be isolated and purified by, for example, the following process:

(1) The culture solution is subjected to centrifugation at 3,000–12,000 rpm. for 30–10 minutes to divide it into solution and precipitates. Then, the precipitates are washed with distilled water and again subjected to the centrifugation. The washings are combined with said solution. This process is repeated 1–5 times (usually 3 times).

(2) The solution thus collected is concentrated by evaporation at a temperature of 10°–30° C. under reduced pressure of 5–30 mmHg for 1–6 hours and the solid matter thus precipitated is washed with distilled water and then dissolved. The solution is concentrated again by evaporation. This process is repeated 1–5 times (usually 3 times) to obtain white, yellow or brownish white crystalline powders, which are soluble in water.

(3) The crystalline powders are fractionated by using a separation means, for example, a molecular sieve such as Sephadex (an adsorptive filtration gel produced by Biochemical Co., Sweden) G-25. Activities of the respective fractions are examined and the active fraction is selected repeatedly. By this process, a substance having a single activity peak is obtained.

The active ingredient is dissolved again in water and purified by a purification means such as ion-exchange chromatography or dialysis.

(4) The active ingredient thus purified can be separated by addition of various organic solvents to the aqueous solution, change of pH from acidic region into alkaline region, salting out followed by reprecipitation and filtration or concentration by evaporation.

The substance has the following properties:

| Thermal stability | Stable (substance does not lose its activity after being maintained at 100° C. for 15 minutes) |
| --- | --- |
| Ninhydrin reaction | (−) |
| Ehrlich reaction | (−) |
| Sakaguchi reaction | (−) |

Antimalignant activity of the active ingredient thus isolated and purified was confirmed as follows by adding a diluted aqueous solution thereof to a culture solution of L-1210 cells, cultivating the same at 35° C. for 48 hours and determining the rate of inhibition of propagation of the cells.

| Degree of dilution (rate) | Rate of inhibition (%) | |
| --- | --- | --- |
|  | Lot A | Lot B |
| 50 | 100 | 100 |
| 100 | 100 | 95.3 |
| 200 | 83.0 | 83.5 |
| 400 | 72.7 | 78.6 |
| 800 | 69.0 | 61.4 |
| 1600 | 59.1 | 56.4 |
| 3200 | 49.9 | — |

Thus, it is apparent that the substance produced by Staphylococcus epidermidis has an effect of controlling various malignant tumors such as liquid cancers and solid cancers. The substance does not exhibit acute toxicity.

(5) Administration of the Active Ingredient

Dosage is about 3–300 mg/kg, though it differs depending on administration route. The culture solution from which solid matter has been removed can be used directly. However, as a matter of course, it is better to use the isolated and purified active ingredient for controlling the dosage precisely. Various administration manners are possible such as intravenous, subcutaneous, intracutaneous or intramuscular injection, peroral administration, suppositories, troches and emulsions. Accordingly, the form of preparations can be selected suitably and may be such as powders, tablets (monolayer tablets, double layer tablets, enteric tablets, etc.), capsules, injections charged in ampoules or vials, sublingual tablets, troches, suppositories or fatty emulsions.

BRIEF DESCRIPTION OF THE DRAWINGS

FIGS. 1-4 show U.V. spectrum and IR spectrum of fractions obtained by a process shown in Example 2.

FIG. 1 shows U.V. spectrum of an active ingredient of a molecular weight of 5,000-10,000 (original solution diluted with water into 1:10 solution);

FIG. 2 shows U.V. spectrum of an active ingredient of a molecular weight of 1,000-5,000 (original solution);

FIG. 3 shows IR spectrum of an active ingredient of a molecular weight of 5,000-10,000; and FIG. 4 shows IR spectrum of an active ingredient of a molecular weight of 1,000-5,000.

The following examples further illustrate the present invention. It is to be understood that the following examples by no means limit the present invention.

EXAMPLE 1

Staphylococcus epidermidis STF was cultivated at 37° C. for 48 hours in a medium of the following composition:

| Corn steep liquor | 6 g |
|---|---|
| $NH_4H_2PO_4$ | 3 g |
| Yeast extract | 2.5 g |
| Dextrose | 10 g |
| $CaCO_3$ | 2.5 g |
| Distilled water | ad 1 liter (pH 4.5) |

The culture solution was subjected to centrifugation at 10,000 rpm. for 30 minutes to divide the same into a supernatant liquid and precipitates. The precipitates were re-dispersed in one liter of distilled water and the dispersion was allowed to stand at 37° C. for 18 hours and was then subjected again to centrifugation at 10,000 rpm. to divide the same into a supernatant liquid and precipitates. This process was repeated five times. The resulting supernatant liquids were combined and concentrated by evaporation under reduced pressure of 10 mmHg at room temperature for about two hours. After about 1/30 concentration was attained, the combined liquid was passed through a layer of Sephadex G-25 and subjected to U.V. spectroanalysis by using an indicator of OD (optical density)$_{265}$. The separation of the fraction involved a method of detecting polysaccharides such as Molisch reaction. A chromatogram of L-1210 cell propagation-inhibition activity was surveyed and active fractions were separated out. This process was repeated three times to obtain the fraction of the highest activity. Aqueous solution of the fraction was concentrated by evaporation to obtain white powders. The powders were washed with water, dissolved again and concentrated by evaporation. This process was repeated five times to obtain white crystalline powders. Yield from one liter of the culture solution was about 0.3 g.

EXAMPLE 2

25 Liters of a liquid medium having the same composition as in Example 1 were prepared. Culture was effected at 37° C. for two days. The culture solution was subjected to centrifugation (6,000 rpm, 20 mins.) to remove the germs. The resulting supernatant liquid (about 23 liters) was concentrated to a volume of about 500 c.c. at 40° C. under reduced pressure.

Figure 1:
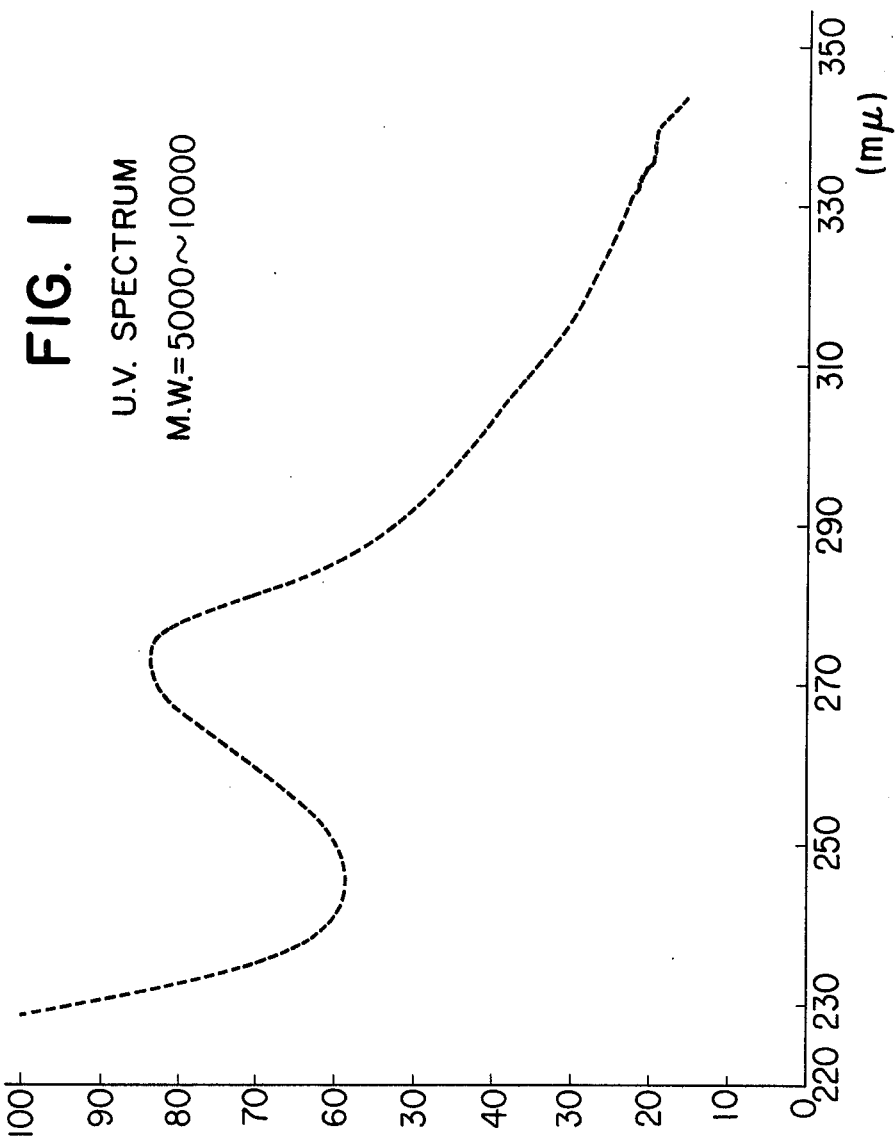
Figure 2:
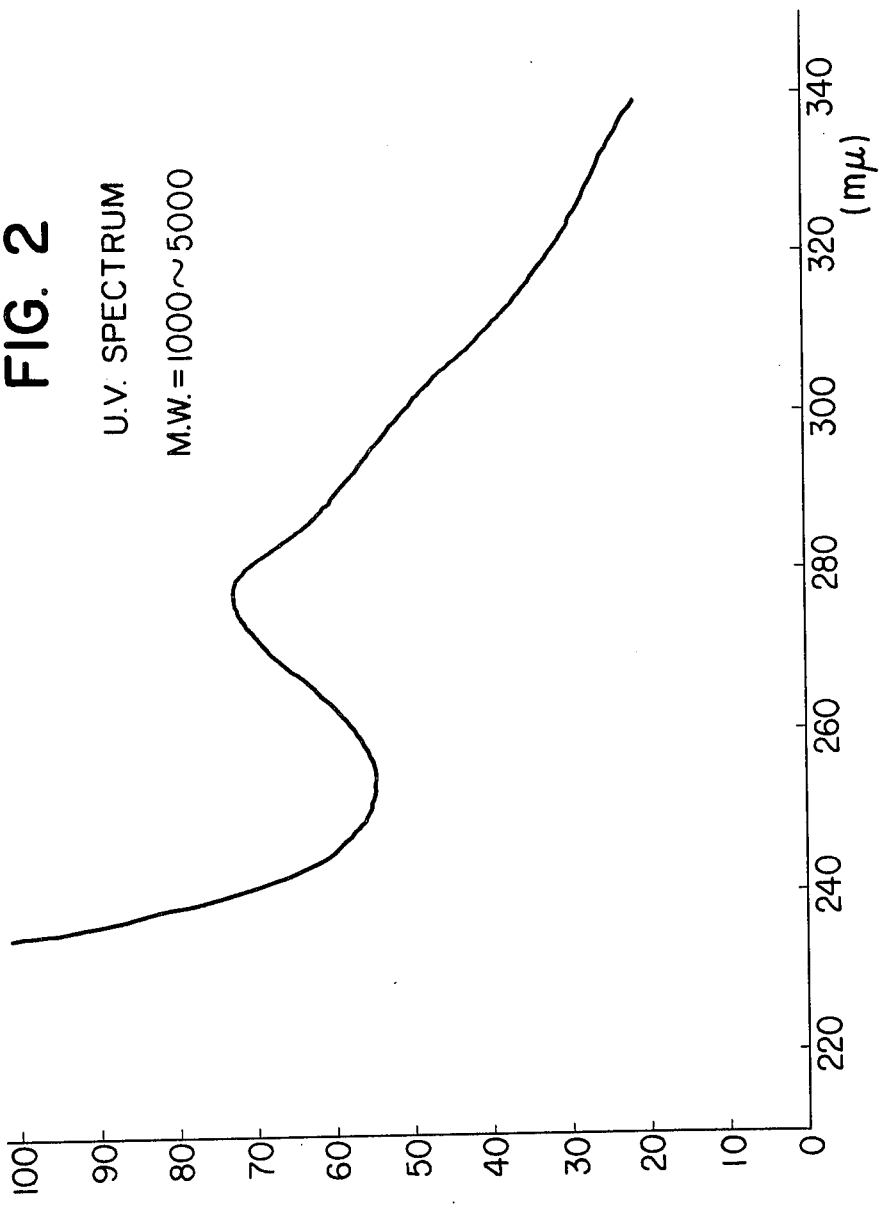
Figure 3:
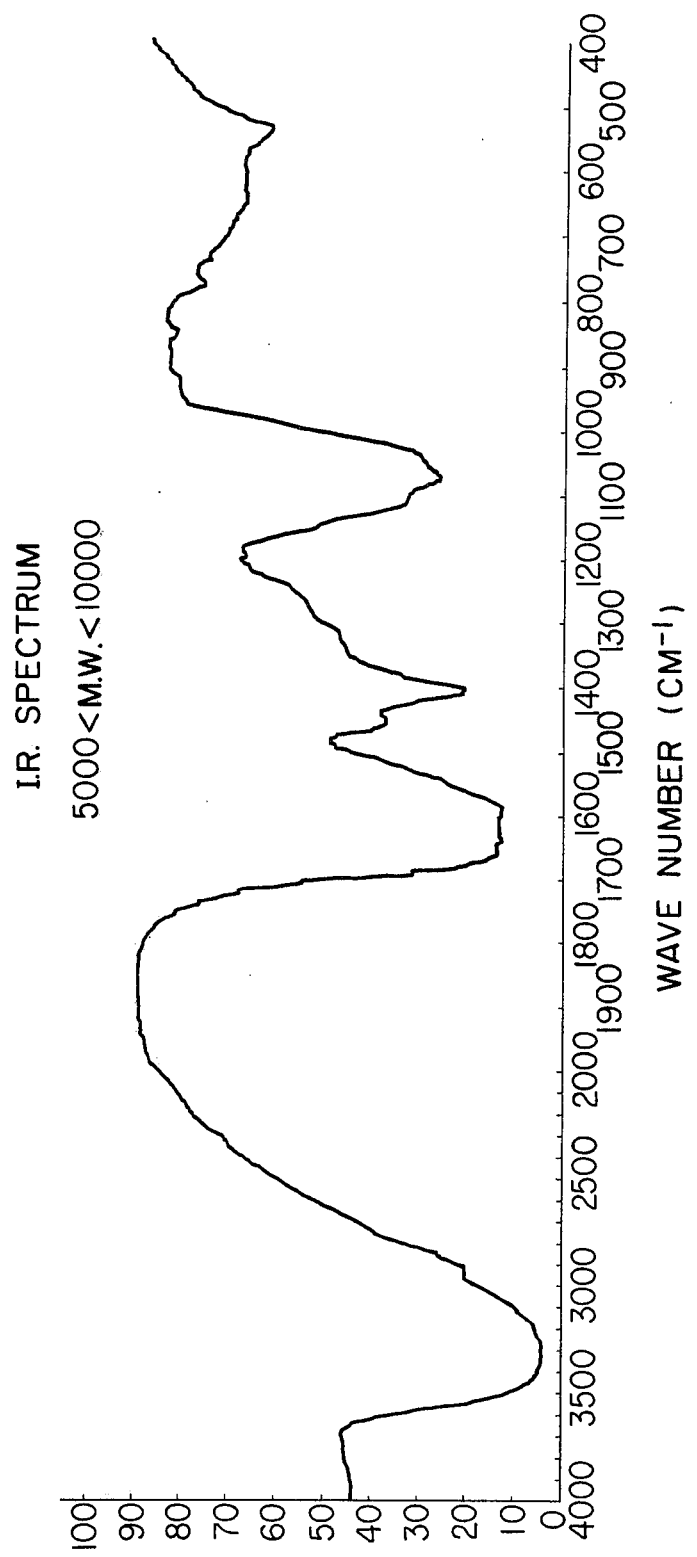

Precipitates thus formed were washed with 100 c.c. of distilled water three times. The washings were combined with the concentrate and the whole was concentrated to a volume of 500 c.c. at 40° C. under reduced pressure. The concentrate was divided into two fractions (one having molecular weights of more than 10,000 and the other having molecular weights of less than 10,000) with Diaflon #10,000 which is a molecular sieve membrane produced by Amicon Far East Ltd. The solution of molecular weights of less than 10,000 was passed through a diethylaminoethyl cellulose column ($OH^-$type) to divide it into acidic substance and neutral and basic substances. Thereafter, the neutral and basic substances were further divided into two fractions (one having molecular weights of 5,000-10,000 (original solution) and the other having molecular weights of less than 5,000) with Diaflon #5000. The fraction of molecular weights of less than 5,000 was further divided into two fractions (one having molecular weights of 1,000-5,000 and the other having molecular weights of less than 1,000) with Diaflon #1000. The concentrate could thus be divided into respective fractions. U.V. Spectrum and IR spectrum of each of the above fractions were determined (See FIGS. 1-4).

Then, the above respective fractions were administered to animals affected by various induced diseases to obtain the following results:

| (A) Antimalignant effects of fractions of 5,000<MW<10,000 and 1,000<MW<5,000 against Leukemia cells L-1210 cultivated in vitro: | | | | |
|---|---|---|---|---|
| Fraction | Conc. (mg/ml) | Average cell number ± Standard deviation ($\times 10^4$/ml) | Rate of inhibition (%) | 50% cell propagation inhibition conc. $IC_{50}$ (mg/ml) |
| Tumor cell control group | 0 | 14.1 ± 0.49 | — | — |
| 1,000<MW<5,000 | 0.25 | 9.9 ± 0.97 | 29.8 | |
| | 0.50 | 8.5 ± 0.19 | 39.7 | |
| | 1.0 | 4.9 ± 0.13 | 65.2 | |
| | 2.0 | 3.7 ± 0.33 | 73.8 | 0.70 |
| 5,000<MW<10,000 | 0.25 | 2.6 ± 0.93 | 81.6 | |
| | 0.50 | 1.8 ± 0.15 | 87.2 | |
| | 1.0 | 0.8 ± 0.001 | 94.3 | <0.25 |

(B) Antimalignant effects of fractions of 5,000<MW<10,000 and 1,000<MW<5,000 against Ehrlich tumor cells cultivated in vitro:

| Fraction | Conc. (mg/ml) | Average cell number ± Standard deviation (×10$^4$/ml) | Rate of inhibition (%) | 50% cell propagation inhibition conc. IC$_{50}$ (mg/ml) |
| --- | --- | --- | --- | --- |
| Tumor cell control group | 0 | 80.4 ± 3.3 | — | — |
| 1,000<MW<5,000 | 0.25 | 58.7 ± 3.7 | 39.9 | |
| | 0.50 | 56.6 ± 3.1 | 43.8 | |
| | 1.00 | 49.7 ± 2.9 | 56.4 | 0.72 |
| | 2.00 | 46.1 ± 2.3 | 63.1 | |
| 5,000<MW<10,000 | 0.25 | 63.2 ± 1.5 | 31.6 | |
| | 0.50 | 52.4 ± 2.5 | 51.5 | 0.48 |
| | 1.00 | 39.4 ± 2.5 | 75.4 | |
| | 2.00 | 37.7 ± 1.8 | 78.5 | |

(C) Antimalignant effects of styeen fractions 5,000<MW<10,000 and 1,000<MW<5,000 against ascites hepatoma cells AH 41C cultivated in vitro:

| Fraction | Conc. (mg/ml) | Average cell number ± Standard deviation (×10$^4$/ml) | Rate of inhibition (%) | 50% cell propagation inhibition conc. IC$_{50}$ (mg/ml) |
| --- | --- | --- | --- | --- |
| Tumor cell control group | 0 | 115.9 ± 1.52 | — | — |
| 1,000<MW<5,000 | 0.1 | 93.4 ± 1.85 | 19.8 | |
| | 0.5 | 93.5 ± 6.60 | 19.0 | |
| | 1.00 | 90.3 ± 2.74 | 22.4 | >2.00 |
| | 2.00 | 87.7 ± 7.94 | 24.1 | |
| 5,000<MW<10,000 | 0.1 | 118.9 ± 2.59 | 0 | |
| | 0.5 | 62.9 ± 3.35 | 45.7 | |
| | 1.00 | 27.3 ± 2.61 | 76.7 | 0.60 |
| | 2.00 | 23.4 ± 1.95 | 80.2 | |

(D) Antimalignant effects of styeen fractions 5,000<MW<10,000 and 1,000<MW<5,000 for mice inoculated with Ehrlich ascites tumor cells (influence on number of the whole tumor cells on the 11th day after the inoculation of the cells):

| Fraction | Amount (mg/kg) | Average whole tumor cells ± standard deviation (×10$^7$) | Rate of inhibition of cell propagation (%) |
| --- | --- | --- | --- |
| Control group | 0 | 115.4 ± 12.6 | — |
| 1,000<MW<5,000 | 200 | 28.4 ± 6.4 | 75.3 |
| | 400 | 31.2 ± 12.5 | 72.9 |
| | 600 | 29.0 ± 3.3 | 74.5 |
| 5,000<MW<10,000 | 200 | 47.1 ± 20.4 | 59.1 |
| | | 55.1 ± 17.1 | 52.2 |
| | | 42.2 ± 5.1 | 63.2 |

What is claimed is:

1. An agent for inhibiting tumor induced by leukemia virus, by inoculation of leukemia cells, by Ehrlich cancer cells and by Sarcoma 180 cells, comprising active substances produced by cultivating *Staphylococcus epidermidis* STF (Bikoken Deposit No. 3706; ATCC 31310) in a nutrient medium containing nitrogen components and inorganic salts, said active substances being crystalline powders, water soluble, stable after heating at 100° C. for 15 minutes, and having a fraction of a molecular weight between 1000 and 5000 exhibiting the ultraviolet spectrum of FIG. 2 and the infrared spectrum of FIG. 4 and a fraction of molecular weight between 5000–10,000 exhibiting the ultraviolet spectrum of FIG. 1 and the infrared spectrum of FIG. 3.

2. A process for preparing an agent for inhibiting tumor induced by leukemia virus, by inoculation of leukemia cells, by Ehrlich cancer cells, by Sarcoma 180 cells, which comprises cultivating *Staphylococcus epidermidis* STF (Bikoken Deposit No. 3706) in a liquid culture medium containing carbon components, nitrogen components and inorganic salts, until said agent is produced in said medium, removing solid matter from the culture solution, concentrating the remaining solution, washing the precipitates thus formed with water, re-dissolving the precipitates, fractionating the solution into a number of fractions by a separation means, selecting a fraction exhibiting said activity, concentrating the fraction, further purifying the fraction and separating the said agent having a molecular weight of 1000–5000.

3. A process for preparing an agent according to claim 2, characterized in that the cultivation is effected at about 37° C.

4. A process for preparing an agent according to claim 2, characterized in that the separation is effected by using an adsorptive filtration gel.

5. A process for preparing an agent according to claim 2, characterized in that the separation is effected by using a molecular sieve.

6. A process for preparing an agent according to claim 2, characterized in that the purification is effected by ion-exchange chromatography.

7. A process for preparing an agent for inhibiting tumors induced by leukemia virus, by inoculation of leukemia cells, by Ehrlich cancer cells, by Sarcoma 180 cells, which comprises cultivating *Staphylococcus epidermidis* STF (Bikoken Deposit No. 3706) in a liquid culture medium containing carbon components, nitrogen components and inorganic salts, until said agent is produced, removing solid matter from the culture solution, concentrating the remaining solution, washing the precipitates thus formed with water, re-dissolving the precipitates, fractionating the solution into a number of fractions by a separation means, selecting a fraction exhibiting said activity, concentrating the fraction, further purifying the fraction and separating the said agent having molecular weight of 5000–10,000.

8. A process for preparing an agent according to claim 7, characterized in that the cultivation is effected at about 37° C.

9. A process for preparing an agent according to claim 7, characterized in that the separation is effected by using an adsorptive filtration gel.

10. A process for preparing an agent according to claim 7, characterized in that the separation is effected by using a molecular sieve.

11. A process for preparing an agent according to claim 7, characterized in that the purification is effected by ion-exchange chromatography.

* * * * *